US00PP19823P3

(12) United States Plant Patent
Giesen

(10) Patent No.: US PP19,823 P3
(45) Date of Patent: Mar. 10, 2009

(54) ***ARGYRANTHEMUM* PLANT NAMED 'SASCOT WHIT'**

(50) Latin Name: *Argyranthemum frutescens*
Varietal Denomination: Sascot Whit

(75) Inventor: Eric Giesen, Andijk (NL)

(73) Assignee: Goldsmith Seeds Europe B.V., Andijk (NL)

( * ) Notice: Subject to any disclaimer, the term of this patent is extended or adjusted under 35 U.S.C. 154(b) by 0 days.

(21) Appl. No.: 11/890,346

(22) Filed: Aug. 6, 2007

(65) Prior Publication Data

US 2009/0044303 P1 Feb. 12, 2009

(51) Int. Cl.
*A01H 5/00* (2006.01)

(52) U.S. Cl. ..... Plt./406

(58) Field of Classification Search ..... Plt./406
See application file for complete search history.

(56) References Cited

PUBLICATIONS

GTITM UPOVROM Citation for Sascot Whit as per CA PBR 06–367; Mar. 21, 2006.*

* cited by examiner

*Primary Examiner*—Kent L Bell
(74) *Attorney, Agent, or Firm*—Jondle & Associates, P.C.

(57) ABSTRACT

A new *Argyranthemum* plant particularly distinguished by its large white inflorescences, a compact and full plant habit, dark green foliage and good vigor is disclosed.

2 Drawing Sheets

Genus and species: *Argyranthemum frutescens.*
Variety denomination: 'Sascot Whit'.

BACKGROUND OF THE NEW PLANT

The present invention comprises a new and distinct cultivar of *Argyranthemum,* botanically known as *Argyranthemum frutescens,* and hereinafter referred to by the cultivar name 'Sascot Whit'. The new cultivar originated from a hybridization made in August 2003 in Andijk, The Netherlands. The female parent was the white flowered *Argyranthemum* plant 'Arg Whit' (U.S. PP18,723), while the male parent was the proprietary white flowered *Argyranthemum* 'AR03-158-2' (unpatented). The seeds produced by the hybridization were sown in January 2004 in Andijk, The Netherlands. A single plant selection was chosen for further evaluation and for asexual propagation in May 2004 in Andijk, The Netherlands.

The new cultivar was created in 2003 in Andijk, The Netherlands and has been asexually reproduced repeatedly by vegetative cuttings and tissue culture in Andijk, The Netherlands and Hillscheid, Germany over a three-year period. The plant has also been trialed at Gilroy, Calif., Andijk, The Netherlands and Hillscheid, Germany. The present invention has been found to retain its distinctive characteristics through successive asexual propagations.

SUMMARY OF THE INVENTION

The following are the most outstanding and distinguishing characteristics of this new cultivar when grown under normal horticultural practices in Gilroy, Calif.

1. Large, white inflorescences;
2. A compact and full plant habit;
3. Dark green foliage; and
4. Good plant vigor.

DESCRIPTION OF THE PHOTOGRAPHS

This new *Argyranthemum* plant is illustrated by the accompanying photographs which show overall plant habit including blooms, buds, and foliage of the plant; the colors shown are as true as can be reasonably obtained by conventional photographic procedures.

Figure 1:
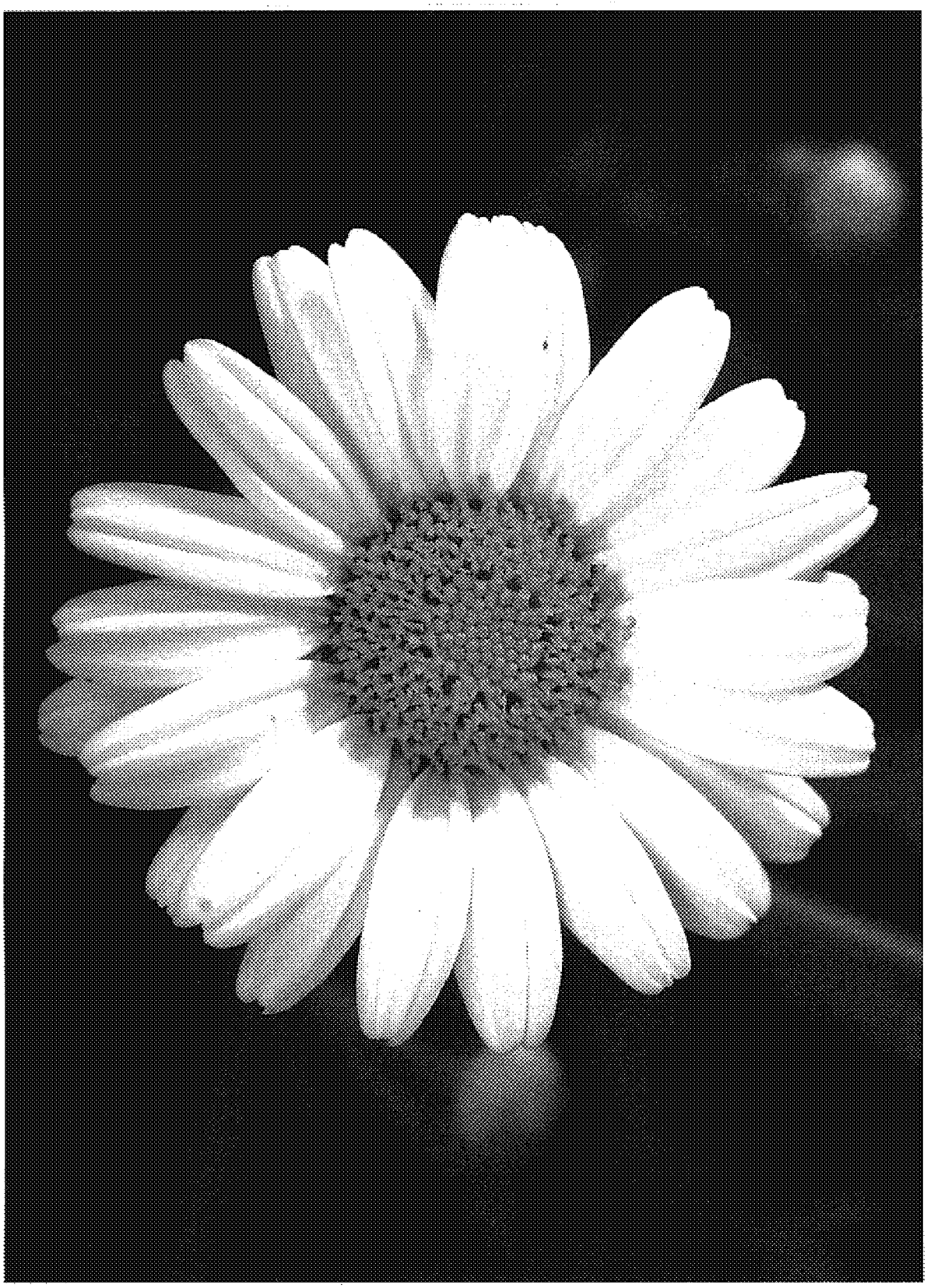

FIG. 1 Close-up of a 3 to 4 month old plant grown in a 5-inch pot in a greenhouse in Andijk, The Netherlands in May.

Figure 2:
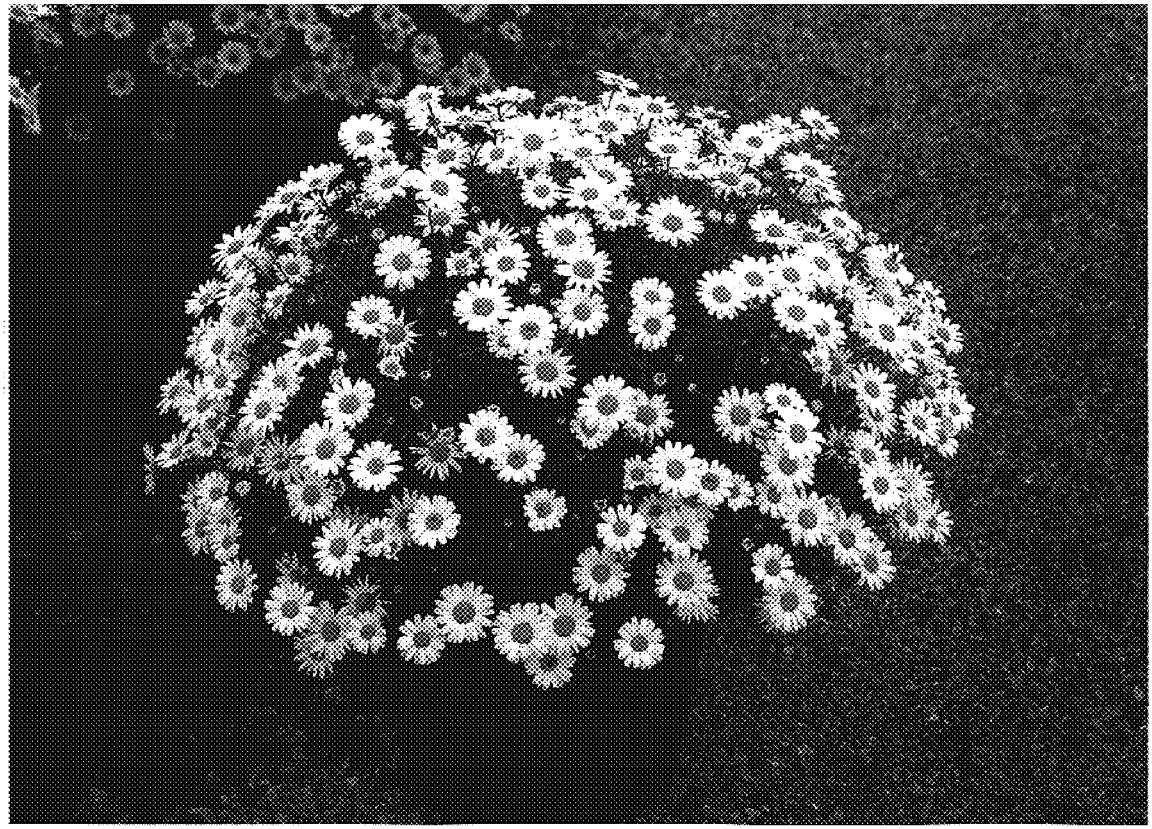

FIG. 2 Overall plant habit including blooms, buds, and foliage of the plant grown outside in a 10-inch basket in the summer in Andijk, The Netherlands in August.

DESCRIPTION OF THE NEW CULTIVAR

The following detailed descriptions set forth the distinctive characteristics of 'Sascot Whit'. The data which define these characteristics were collected from asexual reproductions carried out in Gilroy, Calif. The plant history was taken on twelve-week-old plants grown in 4-inch pots in the spring in a greenhouse. Color readings were taken in the greenhouse in the spring season under natural light. Color references are primarily to the R.H.S. Colour Chart of The Royal Horticultural Society of London (R.H.S.) (2001 edition). Texture description details were observed under a dissecting microscope.

DESCRIPTION OF THE NEW PLANT

Classification:
*Family.*—Asteraceae.
*Botanical name.*—*Argyranthemum frutescens.*
Parentage:
*Female parent.*—'Arg Whit' white-flowered *Argyranthemum* plant (U.S. PP18,723).
*Male parent.*—'AR03-158-2' proprietary white-flowered *Argyranthemum* plant (unpatented).

Growth:

*Form.*—Upright.

*Habit.*—Compact and mounded.

*Growth and branching habit.*—Good, vigorous and freely branching habit.

*Height* (*from top of soil*).—12.0 cm to 14.0 cm.

*Width* (*including inflorescences*).—25.0 cm to 28.0 cm.

*Time to produce a finished flowering plant.*—7 to 9 weeks for a 6-inch pot.

*Outdoor plant performance.*—Used as patio planters, mixed-container plantings, or in garden beds.

*Time to initiate and develop roots.*—21 to 28 days at 68° F. to 74° F.

*Root description.*—Fibrous, freely branching, and white.

Leaves:

*Arrangement.*—Alternate.

*Shape.*—Pinnatifid and deeply divided.

*Apex.*—Acute.

*Base.*—Attenuate.

*Margin.*—Entire.

*Length* (*fully expanded*).—6.5 cm to 7.0 cm.

*Width* (*fully expanded*).—5.0 cm to 5.5 cm.

*Color.*—Immature: Upper surface: RHS 137A. Lower surface: RHS 137A. Mature: Upper surface: RHS 137B. Lower surface: RHS 137A.

*Venation.*—Type: Parallel. Color: RHS 137C.

*Texture.*—Glabrous.

*Petiole.*—Color: RHS 137B. Length: 0.3 cm to 0.4 cm. Width: 0.2 cm. Texture: Glabrous.

Stems:

*Number of branches per plant.*—8 to 10.

*Length* 8.0 cm to 10.0 cm.

*Diameter.*—0.4 cm.

*Internode length.*—0.5 cm to 0.75 cm.

*Color.*—RHS 137C.

*Texture.*—Glabrous.

*Anthocyanin.*—Absent.

Bud:

*Shape.*—Broadly ovate.

*Diameter.*—0.6 cm to 0.8 cm.

*Length.*—0.6 cm to 0.8 cm.

*Color* (*when starting to show color*).—RHS 155B, but a little whiter.

Inflorescence

*Type.*—Terminal and axillary inflorescences held above foliage; capitulum inflorescence on long peduncles.

*Blooming habit.*—Plants flower continuously from the spring through the fall.

*Quantity of inflorescences per plant.*—15 to 31 with 30 buds.

*Lastingness of individual blooms on the plant.*—10 to 14 days.

*Fragrance.*—None.

*Inflorescence diameter.*—4.3 cm to 4.5 cm.

*Depth.*—0.75 cm to 1.0 cm.

*Disc diameter.*—1.3 cm.

*Disc floret.*—Quantity (per inflorescence): 150. Shape: Densely massed, tubular, 5-parted and flared at the apex. Color: RHS 15A. Length: 0.3 cm to 0.4 cm. Diameter (at apex): 0.1 cm. Apex: Acute. Base: Fused.

*Ray floret.*—Quantity: 20 to 22 arranged in one whorl. Shape and form: Ligulate; the corolla consists of a very short tube or funnel at the base and the fused ray florets form one long, elliptically-shaped ray floret which is horizontally (outwards) directed. Length: 1.6 cm to 1.7 cm. Width: 0.5 cm. Color (both mature and immature): Upper surface: RHS 155B, but whiter. Lower surface: RHS 155B, but whiter. Apex: Emarginate. Base: Fused. Margin: Entire. Texture: Papillose.

*Peduncle.*—Color: RHS 143C. Length: 4.0 cm to 5.0 cm. Diameter: 0.15 cm. Texture: Glabrous.

*Involucral bracts.*—Quantity (per inflorescence): 15 to 17. Shape: Ovate. Length: 0.3 cm to 0.35 cm. Width: 0.1 cm. Color: RHS N138B with margins translucent. Apex: Acute. Base: Fused. Margin: Entire. Texture: Glabrous; margins are papery.

Reproductive Organs:

*Androecium.*—Location: Present on disc florets only. Filament length: 0.3 cm to 0.5 cm. Filament color: RHS 1A. Pollen color: RHS 15A. Pollen amount: Moderate.

*Gynoecium.*—Location: Present on ray and disc florets. Pistil length: 0.5 cm. Stigma: Color: RHS 15C. Style: Color: RHS 157B.

Fruit and seed set: Has not been observed.

Disease and insect resistance: Has not been observed.

COMPARISON WITH PARENTAL AND COMMERCIAL CULTIVARS

'Sascot Whit' differs from the female parent, 'Arg Whit' (U.S. PP18,723) in that 'Sascot Whit' has larger inflorescences than 'Arg Whit'. Additionally, 'Sascot Whit' has smaller and darker green foliage and greater plant vigor than 'Arg Whit'.

'Sascot Whit' differs from the male parent, 'AR03-158-2' an unpatented proprietary line, in that 'Sascot Whit' has darker green foliage than 'AR03-158-2'. Additionally, 'Sascot Whit' has a smaller, more compact plant size and thicker branches than 'AR03-158-2'.

'Sascot Whit' differs from the commercial cultivar 'Neptune' (U.S. Plant Pat. No. 13,719) in that 'Sascot Whit' has a more compact and fuller plant habit than 'Neptune'. 'Sascot Whit' has larger inflorescences with more abundant and longer ray florets than 'Neptune'. Additionally, 'Sascot Whit' has shorter peduncles and internodes than 'Neptune'.

I claim:

1. A new and distinct cultivar of *Argyranthemum* plant as shown and described herein.

* * * * *